United States Patent
Lim et al.

(10) Patent No.: US 12,152,125 B2
(45) Date of Patent: Nov. 26, 2024

(54) CROSS-LINKING COMPOUND AND POLYMER USING THE SAME

(71) Applicant: LG Chem, Ltd., Seoul (KR)

(72) Inventors: Won Taeck Lim, Daejeon (KR); Wonmun Choi, Daejeon (KR); Yongjin Kim, Daejeon (KR); Gicheul Kim, Daejeon (KR); Ki Hyun Kim, Daejeon (KR)

(73) Assignee: LG Chem, Ltd., Seoul (KR)

( * ) Notice: Subject to any disclaimer, the term of this patent is extended or adjusted under 35 U.S.C. 154(b) by 764 days.

(21) Appl. No.: 17/271,802

(22) PCT Filed: Jun. 8, 2020

(86) PCT No.: PCT/KR2020/007393
§ 371 (c)(1),
(2) Date: Feb. 26, 2021

(87) PCT Pub. No.: WO2020/251227
PCT Pub. Date: Dec. 17, 2020

(65) Prior Publication Data
US 2021/0324174 A1  Oct. 21, 2021

(30) Foreign Application Priority Data

Jun. 10, 2019  (KR) .................. 10-2019-0068111
May 29, 2020  (KR) .................. 10-2020-0065291

(51) Int. Cl.
*C08K 5/101*  (2006.01)
*C08F 120/06*  (2006.01)
*C08K 5/372*  (2006.01)

(52) U.S. Cl.
CPC ............ *C08K 5/101* (2013.01); *C08F 120/06* (2013.01); *C08K 5/372* (2013.01)

(58) Field of Classification Search
CPC ........ C08K 5/101; C08K 5/372; C08F 120/06
See application file for complete search history.

(56) References Cited

U.S. PATENT DOCUMENTS

| | | | |
|---|---|---|---|
| 4,418,207 | A | 11/1983 | Braun et al. |
| 6,143,821 | A | 11/2000 | Houben |
| 2002/0095016 | A1 | 7/2002 | Siol |
| 2006/0012750 | A1 | 1/2006 | Nakamura et al. |
| 2008/0140037 | A1 | 6/2008 | Newman |
| 2011/0144292 | A1 | 6/2011 | Kojima et al. |
| 2015/0037526 | A1* | 2/2015 | Seth .......... C09J 7/385 428/41.3 |
| 2015/0287993 | A1 | 10/2015 | Komaba et al. |
| 2016/0017187 | A1 | 1/2016 | Lipscomb et al. |
| 2017/0040612 | A1 | 2/2017 | Komaba et al. |

FOREIGN PATENT DOCUMENTS

| | | |
|---|---|---|
| CN | 101094695 A | 12/2007 |
| CN | 104813525 A | 7/2015 |
| CN | 105121579 A | 12/2015 |
| EP | 1354898 A1 | 10/2003 |
| EP | 1439181 A1 | 7/2004 |
| EP | 2083032 A1 | 7/2009 |
| EP | 2986684 A1 | 2/2016 |
| JP | 108165269 A | 6/1996 |
| JP | 2000281737 A | 10/2000 |
| JP | 2002302466 A | 10/2002 |
| JP | 2003011118 A | 1/2003 |
| JP | 2008522003 A | 6/2008 |
| JP | 2012158745 A | 8/2012 |
| KR | 19990071529 A | 9/1999 |
| KR | 101442284 B1 | 9/2014 |
| KR | 20150001272 A | 1/2015 |
| KR | 20150090078 A | 8/2015 |
| KR | 20150143610 A | 12/2015 |
| KR | 20160112220 A | 9/2016 |
| KR | 20160145672 A | 12/2016 |

OTHER PUBLICATIONS

International Search Report for PCT/KR2020/007393 mailed Oct. 7, 2020; 4 pages.
Search Report for European Application No. 20822857.7 dated Oct. 14, 2021. 3 pgs.
Search Report dated Jan. 9, 2023 from the Office Action for Chinese Application No. 202080004400.3 issued Jan. 19, 2023, 2 pages. [See p. 1, categorizing the cited references].
Russell, G. and Li, C., "8-Endo versus 5-exo cyclization of unsaturated acrylate esters upon reaction with t-BuHgl/KI", Tetrahedron Letters, vol. 37, Issue 15, Apr. 1996, pp. 2557-2560.

* cited by examiner

*Primary Examiner* — John E Uselding
(74) *Attorney, Agent, or Firm* — Lerner David LLP

(57) ABSTRACT

The present disclosure relates to a novel cross-linking compound and a polymer using the same. More particularly, the present disclosure relates to a novel cross-linking compound that does not cause thermal decomposition at one end and thus prevents in advance the generation of volatile substances and decomposition products, and a polymer prepared using the same.

6 Claims, No Drawings

CROSS-LINKING COMPOUND AND POLYMER USING THE SAME

TECHNICAL FIELD

Cross-Reference with Related Application(s)

This application claims the benefit of Korean Patent Application No. 10-2019-0068111 filed on Jun. 10, 2019 and Korean Patent Application No. 10-2020-0065291 filed on May 29, 2020 in the Korean Intellectual Property Office, the disclosures of which are incorporated herein by reference in their entity.

The present disclosure relates to a novel cross-linking compound and a polymer using the same. More particularly, the present disclosure relates to a novel cross-linking compound that does not cause thermal decomposition at one end and thus prevents in advance the generation of volatile substances and decomposition products.

BACKGROUND ART

Super absorbent polymer (SAP) is a synthetic polymer material capable of absorbing moisture from about 500 to about 1,000 times its own weight, and each manufacturer has denominated it as different names such as SAM (Super Absorbency Material), AGM (Absorbent Gel Material) or the like. Such a super absorbent polymer started to be practically applied in sanitary products, and now they are widely used for production of hygiene products such as paper diapers for children or sanitary napkins, water retaining soil products for gardening, water stop materials for the civil engineering and construction, sheets for raising seedling, fresh-keeping agents for food distribution fields, materials for poultice or the like.

In most cases, these super absorbent polymers have been widely used in the field of sanitary materials such as diapers or sanitary napkins. For these applications, the super absorbent polymer should exhibit a high moisture absorbency, it should not release the absorbed water even in the external pressure, and additionally it should well retain the shape even in a state where the volume is expanded (swelled) by absorbing water, and thereby exhibit excellent liquid permeability.

Therefore, in order for the super absorbent polymer to have excellent performance, the base polymer, which is a polymer constituting the most important component, should have a high absorption capacity.

In order to make such a base polymer, generally, an acrylic acid-based monomer can be polymerized in the presence of an internal crosslinking agent to control the crosslinking density inside the polymer. The internal crosslinking agent is for crosslinking the inside of a polymer in which an acrylic acid-based monomer is polymerized, that is, a base polymer, and the internal crosslinking density of the base polymer can be adjusted according to the type and content of the internal crosslinking agent. When the crosslinking density of the base polymer is low, the absorption capacity becomes high, but the strength is weak, which may cause a problem that the shape is not maintained in a subsequent process. When the crosslinking density is too high, the strength increases, but the water absorption capacity may decrease, and so it is very important to adjust the appropriate crosslinking density from the viewpoint of the strength and absorption capacity of the base polymer.

In addition, the super absorbent polymer prepared by polymerizing an acrylic acid monomer has a peculiar odor of acrylic acid, and in the case of using in hygiene products such as diapers, an unpleasant odor is also accomplished when excreting body fluids such as urine, and a function of effectively reducing these odors is required. For this purpose, a method of mixing and using a porous adsorption material with a super absorbent polymer has been developed.

However, when the porous adsorption material is mixed with the super absorbent polymer, it has the effect of reducing odor, but there is a problem that physical properties of a super absorbent polymer such as absorbent capacity or transmittance is deteriorated, or a caking phenomenon occurs in which super absorbent polymers agglomerate or solidifies over time.

Meanwhile, Japanese Unexamined Patent Publication No. 2008-522003 discloses a cross-linking compound used in the manufacture of super absorbent polymers. However, when the compound is used as a crosslinking agent including acrylates at both ends, the acrylate ends may be decomposed. At this time, volatile substances such as 2-methyl-1,3-butadiene (VOC; Volatile Organic Compounds) and decomposition products are generated, which may cause generation of odors. Therefore, the need for cross-linking compounds having reduced volatile substances and decomposition products have become conspicuous.

PRIOR ART LITERATURE

Patent Literature (Patent Literature 1) Japanese Unexamined Patent Publication No. 2008-522003

DETAILED DESCRIPTION OF THE INVENTION

Technical Problem

It is an object of the present disclosure to provide a novel cross-linking compound that does not cause thermal decomposition at one end and thus reduces the generation of volatile substances and decomposition products, and a polymer prepared using the same.

Technical Solution

In order to achieve the object, there is provided a cross-linking compound represented by the following Chemical Formula 1.

[Chemical Formula 1]

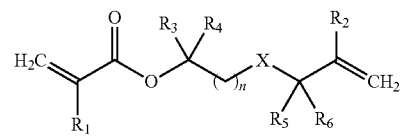

in the Chemical Formula 1,
$R_1$ and $R_2$ are each independently hydrogen or methyl,
$R_3$, $R_4$, $R_5$ and $R_6$ are each independently hydrogen, $C_{1-20}$ alkyl, or $C_{3-20}$ cycloalkyl,
X is O, S, or $CH_2$, and
n is an integer of 2 to 10.

There is also provided a polymer in which the cross-linking compound and an acrylic acid-based monomer are polymerized.

Hereinafter, embodiments of the present disclosure will be described in detail.

As used herein, the term "alkyl" means a saturated, linear or branched, monovalent hydrocarbon having 1 to 20 carbon atoms, preferably 1 to 10 carbon atoms, more preferably 1 to 5 carbon atoms. Examples of the alkyl include methyl, ethyl, propyl, n-propyl, isopropyl, n-butyl, isobutyl, tert-butyl, sec-butyl, 1-methyl-butyl, 1-ethyl-butyl, n-pentyl, isopentyl, neopentyl, tert-pentyl, n-hexyl, isohexyl, 1-methylpentyl, 2-methylpentyl, 4-methyl-2-pentyl, 3,3-dimethylbutyl, 2-ethylbutyl, n-heptyl, 1-methylhexyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, 2-methylpentyl, 4-methylhexyl, 5-methylhexyl, and the like, but the present disclosure is not limited thereto.

As used herein, the term "cycloalkyl" means a saturated, aliphatic cyclic monovalent hydrocarbon having 3 to 20 carbon atoms, preferably 3 to 10 carbon atoms, more preferably 5 to 10 carbon atoms. Examples of the cycloalkyl include cyclopropyl, cyclobutyl, cyclopentyl, cyclohexyl, and the like, but the present disclosure is not limited thereto.

Cross-Linking Compound

The cross-linking compound according to one embodiment of the present disclosure is represented by Chemical Formula 1.

Preferably, the $R_1$ and $R_2$ may be hydrogen.

Preferably, the $R_3$, $R_4$, $R_5$ and $R_6$ may be each independently hydrogen, $C_{1-10}$ alkyl, or $C_{3-10}$ cycloalkyl, More preferably, the $R_3$, $R_4$, $R_5$ and $R_6$ may be each independently hydrogen or $C_{1-10}$ alkyl, Most preferably, the $R_3$, $R_4$, $R_5$ and $R_6$ may be each independently hydrogen or methyl.

Preferably, the $R_3$ and $R_4$ may be methyl.

Preferably, the $R_5$ and $R_6$ may be each independently hydrogen or methyl, and at least one of $R_5$ and $R_6$ may be hydrogen.

Preferably, the $R_3$ and $R_4$ may be methyl, the $R_5$ and $R_6$ may be each independently hydrogen or methyl, and at least one of $R_5$ and $R_6$ may be hydrogen.

Preferably, X may be O, or $CH_2$.

Preferably, the n may be an integer of 2 to 5.

More preferably, the n may be 2 or 3,

Most preferably, the n may be 2.

According to one embodiment of the present disclosure, the compound represented by Chemical Formula 1 may be represented by any of the following Chemical Formulas 1-1 to 1-4, but the present disclosure is not limited thereto.

[Chemical Formula 1-1]

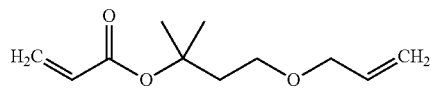

[Chemical Formula 1-2]

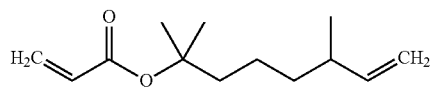

[Chemical Formula 1-3]

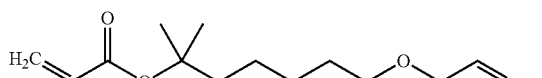

[Chemical Formula 1-4]

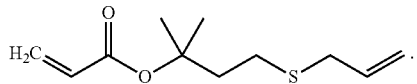

The use of the compound represented by Chemical Formula 1 is not limited thereto, and it may be used as a crosslinking agent during polymerization with an acrylic acid-based monomer in the process of preparing a super absorbent polymer.

One end of the cross-linking compound represented by Chemical Formula 1 includes an acrylate that is decomposed by heat, but the other end includes an alkenyl which is not decomposed by heat. Therefore, the acrylate end is thermally decomposed upon heating, but at the alkenyl end, the decomposition of the cross-linking compound does not occur, and thus, the amount of volatile organic compounds (VOC) and decomposition products that cause odors is reduced, and thereby, it can prevent generation of odors when used as a super absorbent polymer or the like.

The cross-linking compound of Chemical Formula 1 can be prepared by a known organic synthesis method. For example, it can be prepared by the method as in Reaction Scheme 1 below, but the present disclosure is not limited thereto.

[Reaction Scheme 1]

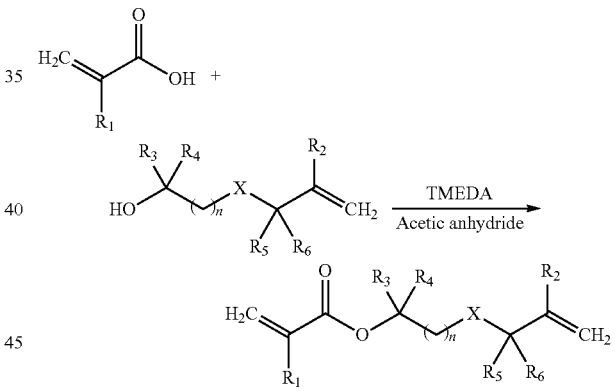

in the Reaction Scheme 1, $R_1$ to $R_6$, X and n are the same as defined in Chemical Formula 1.

Polymer

According to another embodiment of the present disclosure, there is provided a polymer in which the compound represented by Chemical Formula 1 and an acrylic acid-based monomer are crosslinked and polymerized.

The acrylic acid-based monomer is a compound represented by the following Chemical Formula 2.

R—COOM                   [Chemical Formula 2]

in the Chemical Formula 2,

R is an alkyl group having 2 to 5 carbon atoms and containing an unsaturated bond, and M is a hydrogen atom, a monovalent or divalent metal, an ammonium group or an organic amine salt.

Preferably, the acrylic acid-based monomer may include at least one selected from the group consisting of acrylic acid, methacrylic acid, and monovalent metallic salt, divalent metallic salt, ammonium salt, or organic amine salt thereof.

The acrylic acid-based monomer may be those having acidic groups which are at least partially neutralized.

As used herein, the term "polymer" or "crosslinked polymer" means being in a state wherein acrylic acid-based monomers are polymerized in the presence of the cross-linking compound of Chemical Formula 1, and may include all the water content ranges or particle size ranges. Among the polymers, a polymer in a state after polymerization and before drying, having a water content (moisture content) of about 40% by weight or more may be designed as a hydrogel polymer.

And, "base polymer" or "base polymer powder" means those made in the form of powder by drying and pulverizing the polymer, which means a polymer in a state wherein a crosslinked structure is not formed on the surface of the polymer before the surface crosslinking step is performed.

The cross-linking compound represented by Chemical Formula 1 is a thermally decomposable internal crosslinking agent whose one end is an acrylate, and the internal cross-linking structure of the polymer of which the compound of Chemical Formula 1 and the acrylic acid-based monomer are crosslinked and polymerized may be decomposed by heat (e.g., at 180° C. or higher). Accordingly, crosslinking polymerization of the acrylic acid-based monomer in the presence of the cross-linking compound of Chemical Formula 1 may provide a crosslinked polymer into which a thermally decomposable internal crosslinked structure is introduced.

Subsequently, if such a crosslinked polymer is introduced into a high temperature subsequent process, such as a surface crosslinking process, the crosslinked structure derived from the compound of Chemical Formula 1 in the crosslinked polymer is at least partially decomposed. Consequently, the internal crosslinking density in the cross-linked polymer is reduced. Meanwhile, the surface of the crosslinked polymer is additionally crosslinked by a surface crosslinking agent, so that the external crosslinking density is increased. Therefore, crosslinking polymerization of the acrylic acid monomer is performed in the presence of the cross-linking compound represented by Chemical Formula 1 to prepare a base polymer. When the base polymer is subjected to a subsequent process such as surface crosslinking, the internal crosslinked structure in the crosslinked polymer is decomposed, and the surface of the crosslinked polymer can be additionally crosslinked to obtain a super absorbent polymer whose crosslinking density increases from the inside to the outside of the polymer.

The super absorbent polymer thus prepared may have a reduced internal crosslinking density than the base polymer of the existing super absorbent polymer. Thereby, the super absorbent polymer can exhibit a relatively improved centrifuge retention capacity as compared with the existing super absorbent polymer.

Further, the super absorbent polymer may have a thicker surface crosslinked layer than the existing super absorbent polymer after internal crosslinking bond is decomposed or by proceeding surface crosslinking while being decomposed. Thereby, the super absorbent polymer can exhibit excellent absorbency under pressure. Therefore, unlike the conventional common sense that the super absorbent polymer of one embodiment has an inverse relationship between the centrifuge retention capacity and the absorbency under pressure as the crosslinking density increases from the inside to the outside, various physical properties such as centrifuge retention capacity and absorbency under pressure can be improved together, and thus all exhibit excellent properties.

Meanwhile, the cross-linking compound represented by Chemical Formula 1 is an internal crosslinking agent for reducing the generation of volatile substances (VOC; Volatile Organic Compounds) and decomposition products and includes alkenyl, which is not decomposed at one end of the cross-linking compound even when heated.

The conventional cross-linking compound has a diacrylate structure, and the acrylate is provided with an internal crosslinked structure, which serves to decompose by heat in the process of preparing a super absorbent polymer. At this time, the acrylate remaining before/after decomposition is subjected to hydration reaction with water, and fallen off and vaporized from the super absorbent polymer to generate volatile substances (VOC; Volatile Organic Compounds) and decomposition products, which may cause odors.

However, the cross-linking compound represented by Chemical Formula 1 of the present disclosure includes an alkenyl structure that has not been thermally decomposed at the end, unlike a conventional cross-linking compound, and thereby reduces the cause of the falling-off and vaporization.

Thus, according to one embodiment of the present disclosure, for the polymer in which the cross-linking compound represented by Chemical Formula 1 and the acrylic acid-based monomer is crosslinked and polymerized, the total sum of the amount of generation of major volatile substances (VOC; Volatile Organic Compounds) and decomposition products, for example, MeOH, C4, 2-methyl-1,3-butadiene, 2-methyl-3-buten-2-ol, 3-methyl-3-buten-1-ol, etc. may be 50 ppm or less, 30 ppm or less, 20 ppm or less, or 10 ppm or less. Here, the C4 is collectively referred to as a hydrocarbon compound of various structures having 4 to 10 carbon atoms.

The amount of the main volatile substances and decomposition products generated is measured by placing 0.5 g of a super absorbent polymer in 500 ml of 0.9 wt % NaCl aqueous solution, heating only 2 ml of them at 80° C. for 1 hour, and analyzing volatile substances and decomposition products gas with Headspace-GC/MS.

Further, the polymer may be those wherein a conventionally known crosslinking agent is further crosslinked, in addition to the cross-linking compound represented by Chemical Formula 1.

As such a conventional internal crosslinking agent, a compound containing two or more crosslinkable functional groups in a molecule can be used. Specific examples of the conventional internal crosslinking agent may include one or more selected from the group consisting of N,N'-methylenebisacrylamide, trimethylolpropane tri(meth)acrylate, ethylene glycol di(meth)acrylate, polyethylene glycol(meth)acrylate, propylene glycol di(meth)acrylate, polypropylene glycol(meth)acrylate, butanediol di(meth)acrylate, butylene glycol di(meth)acrylate, diethylene glycol di(meth)acrylate, hexanediol di(meth)acrylate, triethylene glycol di(meth)acrylate, tripropylene glycol di(meth)acrylate, tetraethylene glycoldi(meth)acrylate, dipentaerythritol pentaacrylate, glycerin tri(meth)acrylate, pentaerythritol tetraacrylate, triarylamine, ethylene glycol diglycidyl ether, propylene glycol, glycerin, and ethylene carbonate, but the present disclosure is not limited thereto.

As described above, due to the structural properties of the novel cross-linking compound of Chemical Formula 1, the polymer of the present disclosure reduces the amount of volatile substances (VOC; Volatile Organic Compounds) and decomposition products generated in the preparation process of the super absorbent polymer, despite the thermally decomposable internal crosslinked structure, and prevent generation of odors while having various physical properties such as centrifuge retention capacity and absorbency under pressure which are equivalent to those of the super absorbent polymer using a crosslinking agent having acrylate at both ends. Thus, it exhibits a deodorant performance that reduces the odor peculiar to the super absorbent polymer and/or the malodor generated in hygiene products even without the addition of a separate additive, and can provide an excellent usability.

Accordingly, the super absorbent polymer may provide hygiene products such as diapers that exhibit excellent absorption properties even after undergoing a high-temperature production process.

Advantageous Effects

The cross-linking compound of the present disclosure is a compound having a novel structure which has not been known in the past, and contains an alkenyl at one end, and does not cause thermal decomposition at the end, and therefore, reduces the generation of volitable substances (VOC; volatile organic compounds) and decomposition products, so that generation of odors can be prevented.

Therefore, the polymer in which the cross-linking compound of the present disclosure and the acrylic acid-based monomer are polymerized has the same level of centrifuge retention capacity and absorbency under pressure as that of a conventional thermally decomposable crosslinking agent, and at the same time, can reduce the generation amount of volatile substances generated during use (VOC; Volatile Organic Compounds) and the decomposition products, thereby preventing the generation of odors.

DETAILED DESCRIPTION OF THE EMBODIMENTS

Hereinafter, embodiments of the present disclosure will be described in more detail in order to assist in understanding of the invention. However, these examples are for illustrative purposes only and are not intended to limit the scope of the present disclosure.

Example 1: Synthesis of 4-(allyloxy)-2-methylbutan-2-yl acrylate

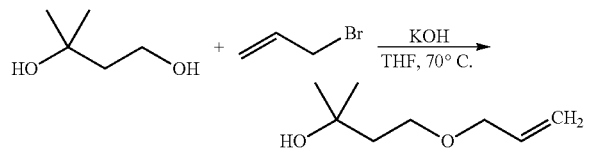

KOH (2.0 g, 36 mmol, 1.2 eq) was put in THF, and the mixture was refluxed and all dissolved. After all KOH was dissolved, 3-methylbutane-1,3-diol (3.1 g, 30 mmol, 1 eq) was slowly added, paying attention not to raise the temperature. After stirring for about 30 minutes, ally 1 bromide (4.4 g, 36 mmol, 1.2 eq) was slowly added, paying attention not to raise the temperature. Then, the reaction solution was stirred under reflux at 70° C. for 16 hours. After determining the completion of the reaction using TLC, NH$_4$Cl aqueous solution was added and subjected to a neutralization reaction to terminate the reaction. THF was removed by distillation under reduced pressure, and the extraction using EA was repeated 3 times, and the obtained EA layer was washed with water. Residual water was removed using MgSO$_4$, distilled under reduced pressure, and then concentrated to obtain 4-(allyloxy)-2-methylbutan-2-ol (yield: 88%).

1H NMR (CDCl$_3$, 500 MHz): 5.91 (m, 1H), 5.27 (m, 1H), 5.19 (m, 1H), 3.99 (ddd, J=5.62 Hz, 1.47 Hz, 1.46 Hz, 2H), 3.68 (t, J=6.11 Hz, 2H), 3.17 (s, 1H), 1.78 (t, J=6.11 Hz, 2H), 1.26 (s, 6H)

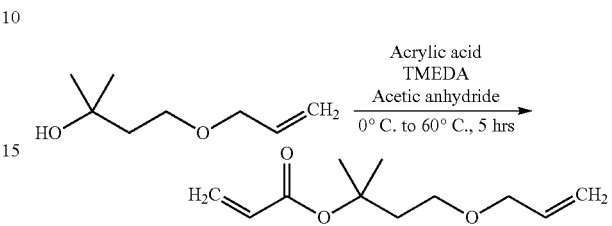

4-(Allyloxy)-2-methylbutan-2-ol (1.4 g, 10 mmol, 1 eq) and acrylic acid (1.4 g, 20 mmol, 2 eq) were put into a flask, and slowly stirred in an ice bath, and then TMEDA (1.2 g, 10 mmol, 1 eq) was added, paying attention to heat generation. The reaction vessel was transferred to a 60° C. oil bath, and then acetic anhydride (1.3 g, 12.5 mmol, 1.25 eq) was slowly added for 2 hours. Then, the mixture was stirred at 60° C. for 5 hours, and the completion of the reaction was determined using TLC and GC, to which hexane was added, stirred and extracted. After separating the upper hexane layer separately, the lower organic salt layer was extracted with hexane once more, and the hexane layers were collected and washed with water. Residual water in the hexane layer was removed using MgSO$_4$ and distilled under reduced pressure to obtain 4-(allyloxy)-2-methylbutan-2-yl acrylate (yield: 79%).

1H NMR (CDCl$_3$, 500 MHz): 6.30 (dd, J=17.1 Hz, 1.47 Hz, 1H), 6.03 (dd, J=17.1 Hz, 10.5 Hz, 1H), 5.90 (m, 1H), 5.73 (dd, J=10.5 Hz, 1.5 Hz, 1H), 5.26 (ddt, J=17.6 Hz, 1.7 Hz, 1.4 Hz, 1H), 5.16 (ddt, J=17.6 Hz, 1.7 Hz, 1.4 Hz, 1H), 3.95 (dt, 5.6 Hz, 1.2 Hz, 2H), 3.54 (t, J=6.8 Hz, 2H), 2.13 (t, J=6.8 Hz, 2H), 1.52 (s, 6H).

Example 2: Synthesis of 2,6-dimethyloct-7-en-2-yl acrylate

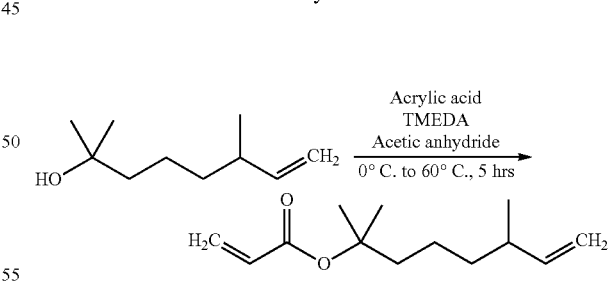

2,6-Dimethyloct-7-en-2-ol (1.6 g, 10 mmol, 1 eq) and acrylic acid (1.4 g, 20 mmol, 2 eq) were put into a flask, and slowly stirred in an ice bath, and then TMEDA (1.2 g, 10 mmol, 1 eq) was added, paying attention to heat generation. The reaction vessel was transferred to a 60° C. oil bath, and then acetic anhydride (1.3 g, 12.5 mmol, 1.25 eq) was slowly added for 2 hours. Then, the mixture was stirred at 60° C. for 5 hours, and the completion of the reaction was determined using TLC and GC, to which hexane was added, stirred and extracted. After separating the upper hexane layer separately, the lower organic salt layer was extracted with hexane once more, and the hexane layers were collected and washed with water. Residual water in the hexane layer was removed using MgSO$_4$ and distilled under reduced pressure to obtain 2,6-dimethyloct-7-en-2-yl acrylate (yield: 79%).

1H NMR (CDCl$_3$, 500 MHz): 6.29 (dd, J=17.4 Hz, 1.47 Hz, 1H), 6.03 (dd, J=17.4 Hz, 10.3 Hz, 1H), 5.72 (dd, J=10.5 Hz, 1.7 Hz, 1H), 5.67 (m, 1H), 4.95 (m, 2H), 4.90 (m, 2H), 2.12 (m, 1H), 1.75 (m, 2H), 1.46 (s, 6H), 1.30 (m, 4H), 0.97 (d, J=6.8 Hz, 3H)

Example 3: Synthesis of 7-(allyloxy)-2-methylheptan-2-yl acrylate

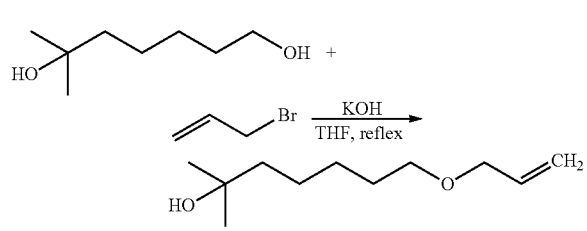

KOH (2.0 g, 36 mmol, 1.2 eq) was put in THF, and the mixture was refluxed and all dissolved. After all KOH was dissolved, 6-methylheptane-1,6-diol (4.4 g, 30 mmol, 1 eq) was slowly added, paying attention not to raise the temperature. After stirring for about 30 minutes, allyl bromide (4.4 g, 36 mmol, 1.2 eq) was slowly added, paying attention not to raise the temperature. Then, the reaction solution was stirred under reflux at 70° C. for 16 hours. After determining the completion of the reaction using TLC, the NH$_4$Cl aqueous solution was added and subjected to a neutralization reaction to terminate the reaction. THF was removed by distillation under reduced pressure, and the extraction using EA was repeated 3 times, and the obtained EA layer was washed with water. Residual water was removed using MgSO$_4$, distilled under reduced pressure, and then concentrated to obtain 7-(allyloxy)-2-methylheptan-2-ol (yield: 82%).

1H NMR (CDCl$_3$, 500 MHz): 5.95 (m, 1H), 5.29 (m, 1H), 5.18 (m, 1H), 3.96 (m, 2H), 3.43 (t, J=6.85 Hz, 2H), 1.61 (m, 2H), 1.47 (m, 2H), 1.36 (m, 4H), 1.21 (s, 6H)

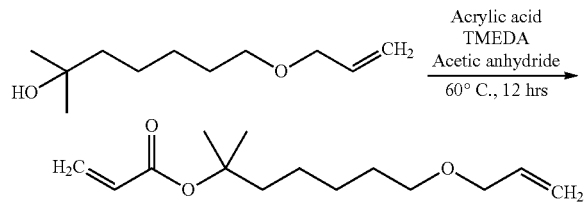

7-(Allyloxy)-2-methylheptan-2-ol (1.9 g, 10 mmol, 1 eq) and acrylic acid (1.4 g, 20 mmol, 2 eq) were put into a flask, and slowly stirred in an ice bath, and then TMEDA (1.2 g, 10 mmol, 1 eq) was added, paying attention to heat generation. The reaction vessel was transferred to a 60° C. oil bath, and then acetic anhydride (1.3 g, 12.5 mmol, 1.25 eq) was slowly added for 2 hours. Then, the mixture was stirred at 60° C. for 12 hours, and the completion of the reaction was determined using TLC and GC, to which hexane was added, stirred and extracted. After separating the upper hexane layer separately, the lower organic salt layer was extracted with hexane once more, and the hexane layers were collected and washed with water. Residual water in the hexane layer was removed using MgSO$_4$ and distilled under reduced pressure to obtain 7-(allyloxy)-2-methylheptan-2-yl acrylate (yield: 87%).

1H NMR (CDCl$_3$, 500 MHz): 6.30 (m, 1H), 6.05 (m, 1H), 5.90 (m, 1H), 5.74 (m, 1H), 5.30 (m, 1H), 5.19 (m, 1H) 3.98 (m, 2H), 3.45 (m, 2H), 1.81 (m, 2H), 1.63 (m, 2H), 1.50 (s, 6H), 1.37 (m, 4H).

Example 4: Synthesis of 4-(allylthio)-2-methylbutan-2-yl acrylate

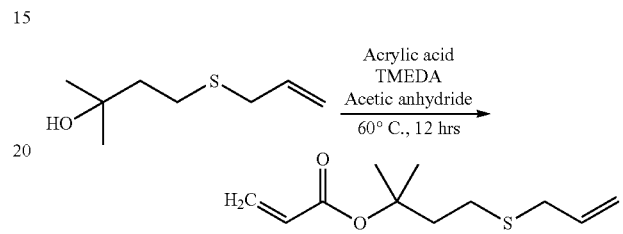

4-(Allylthio)-2-methylbutan-2-ol (1.6 g, 10 mmol, 1 eq) and Acrylic acid (1.4 g, 20 mmol, 2 eq) were put into a flask, and slowly stirred in an ice bath, and then TMEDA (1.2 g, 10 mmol, 1 eq) was added, paying attention to heat generation. The reaction vessel was transferred to a 60° C. oil bath, and then acetic anhydride (1.3 g, 12.5 mmol, 1.25 eq) was slowly added for 2 hours. Then, the mixture was stirred at 60° C. for 12 hours, and the completion of the reaction was determined using TLC and GC, to which hexane was added, stirred and extracted. After separating the upper hexane layer separately, the lower organic salt layer was extracted with hexane once more, and the hexane layers were collected and washed with water. Residual water in the hexane layer was removed using MgSO$_4$ and distilled under reduced pressure to obtain 4-(allylthio)-2-methylbutan-2-yl acrylate (yield: 66%).

1H NMR (CDCl$_3$, 500 MHz): 6.40 (m, 1H), 6.11 (m, 1H), 6.02 (m, 1H), 5.89 (m, 1H), 5.29 (m, 1H), 5.04 (m, 1H), 3.11 (m, 2H) 2.48 (m, 2H), 1.81 (m, 2H), 1.50 (s, 6H).

Example 5

100 g of acrylic acid, 0.6 g of the crosslinking agent of Example 1 as an internal crosslinking agent, 0.008 g of Irgacure TPO (diphenyl(2,4,6-trimethylbenzoyl)phosphine oxide), 0.18 g of laponite and 55 g of water were injected into a glass reactor, Then, 123.5 g of a 32 wt % caustic soda solution was slowly added dropwise to the glass reactor and mixed.

When the caustic soda solution was added dropwise, the temperature of the mixed solution increased due to neutralization heat, and waited for the mixed solution to be cooled. When the temperature of the mixed solution was cooled to about 40° C., 0.2 g of sodium persulfate was added to the mixed solution to prepare a monomer mixture.

The monomer mixture was fed at a speed of 500 to 2000 mL/min on a conveyor belt in which a belt having a width of 10 cm and a length of 2 m was rotated at a speed of 50 cm/min. Then, simultaneously with the supply of the monomer mixture, ultraviolet rays having an intensity of 10 mW/cm$^2$ were irradiated to carry out a polymerization reaction for 60 seconds.

Then, the polymer obtained by the polymerization reaction was prepared into a crump by passing through a hole having a diameter of 10 mm using a meat chopper. Then, using an oven capable of shifting airflow up and down, the crumbs were uniformly dried by flowing hot air at 185° C. from the bottom to the top for 20 minutes and again from the top to the bottom for 20 minutes. The dried crumbs were pulverized using a pulverizing device and then classified to obtain a base polymer having a size of 150 to 850 μm.

A mixed solution of 3.2 g of ultrapure water, 4.0 g of methanol, 0.088 g of ethylene carbonate, and 0.01 g of silica (trade name: REOLOSIL DM30S, manufacturer: Tokuyama Corporation) was put in 100 g of the above-prepared base polymer, and mixed for 1 minute, and then a surface crosslinking reaction was carried out at 185° C. for 90 minutes.

Then, the obtained product was pulverized and classified to obtain a super absorbent polymer having a particle size of 150 to 850 μm.

Example 6

A super absorbent polymer was prepared in the same manner as in Example 3, except that 0.6 g of the crosslinking agent of Example 2 was used instead of the crosslinking agent of Example 1 as the internal crosslinking agent.

Example 7

A super absorbent polymer was prepared in the same manner as in Example 3, except that 0.6 g of the crosslinking agent of Example 3 was used instead of the crosslinking agent of Example 1 as the internal crosslinking agent.

Example 8

A super absorbent polymer was prepared in the same manner as in Example 3, except that 0.6 g of the crosslinking agent of Example 4 was used instead of the crosslinking agent of Example 1 as the internal crosslinking agent.

Comparative Example 1

A super absorbent polymer 2 was prepared in the same manner as in Example 3, except that 0.6 g of 3-methylbutane-1,3-diyldiacrylate was used instead of the crosslinking agent of Example 1 as the internal crosslinking agent. The structure of 3-methylbutane-1,3-diyl diacrylate is as follows.

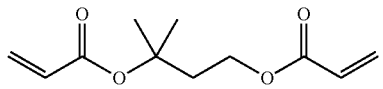

Experimental Example: Evaluation of Generation of Volatile Substances and Decomposition Products In the polymer in which the cross-linking compound of the present disclosure and the acrylic acid-based monomer were polymerized, in order to evaluate whether volatile substances and decomposition products were generated due to thermal decomposition, the amounts of major volatile substances and decomposition products generated after heating the super absorbent polymers of Examples 3, 4 and Comparative Example at 80° C. were measured by HS-GC/MS, and are shown in Table 1 below.

Specifically, 4.5 g of NaCl was put in a 500 ml volumetric flask, and diluted with distilled water to the scale to prepare a 0.9 wt % NaCl aqueous solution. 0.5 g of the super absorbent polymer was added to the NaCl aqueous solution, and then 2 ml of the solution was added to a Headspace Vial (20 ml). The vial was put in an oven, heated to 80° C. for 1 hour, then cooled for 30 minutes, put in an auto-sampler, and the content of the main odor-generating component was analyzed by HS-GC/MS (HS (headspace): Tekmar, GC/MS: SHIMADZU). The analyzed main volatiles and decomposition products were converted in units of ppm and shown in Table 1 below.

TABLE 1

| Main volatile substances and decomposition products (1 ppm or more) | Example 5 | Example 6 | Example 7 | Example 8 | Comparative Example 1 |
| --- | --- | --- | --- | --- | --- |
| MeOH + C4 | — | — | — | — | 1.6 |
| 2-Methyl-1,3-Butadiene | 6.4 | — | — | — | 82.3 |
| 2-Methyl-3-Buten-2-ol | — | — | — | — | 2.2 |
| 3-Methyl-3-Buten-1-ol | — | — | — | — | 7.8 |

As can be seen from Table 1, in Examples 3 to 8, which are super absorbent resins prepared using the cross-linking compound of the present disclosure, the types of main volatile substances and decomposition products were markedly small or were not detected at all, as compared with Comparative Example 1 in which a substance having an acrylate at both ends was used as the crosslinking agent.

In addition, the total amount of volatile substances and decomposition products generated in respective Examples was less than 10% of that of Comparative Example 1, confirming that one embodiment of the present disclosure was remarkably superior in terms of the generation of volatile substances and decomposition products.

The invention claimed is:
1. A cross-linking compound represented by the following Chemical Formula 1:

[Chemical Formula 1]

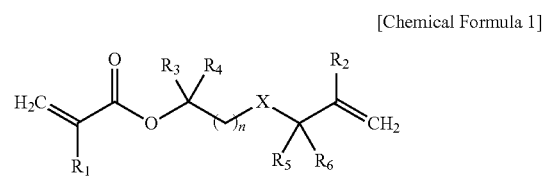

wherein in the Chemical Formula 1,
R1 and R2 are each independently hydrogen,
R3 and R4 are methyl,
R5 and R6 are each independently hydrogen,
X is S, and
n is 2.

2. A polymer comprising the cross-linking compound of claim 1 and an acrylic acid-based monomer, wherein the cross-linking compound of claim 1 and the acrylic acid-based monomer are polymerized.

3. The polymer of claim 2,
wherein the acrylic acid-based monomer is represented by the following Chemical Formula 2:

R—COOM [Chemical Formula 2]

wherein in the Chemical Formula 2,
R is an alkyl group having 2 to 5 carbon atoms and containing an unsaturated bond, and M is a hydrogen atom, a monovalent or divalent metal, an ammonium group or an organic amine salt.

4. The cross-linking compound of claim 1, wherein Chemical Formula 1 is used as a crosslinking agent during polymerization with an acrylic acid-based monomer in preparing a super absorbent polymer.

5. The cross-linking compound of claim 1, wherein one end of the cross-linking compound represented by Chemical Formula 1 includes an acrylate or an acrylate end that is decomposed by heat, and another end of the cross-linking compound includes an alkenyl or an alkenyl end that is not decomposed by heat.

6. The cross-linking compound of claim 5, wherein the acrylate end is thermally decomposed upon heating and the alkenyl end the decomposition of the cross-linking compound does not occur for preventing generation of odors when used in a super absorbent polymer.

* * * * *